United States Patent [19]  
Morrison

[11] Patent Number: 4,719,221  
[45] Date of Patent: Jan. 12, 1988

[54] 2-ACETYLPYRIMIDINE-5-[(DIMETHYLAMINO)THIOCARBONYL]THIOCARBONOHYDRAZONE AND SALTS THEREOF

[75] Inventor: Jr. Morrison, Raleigh, N.C.

[73] Assignee: Burroughs Wellcome Co., Research Triangle Park, N.C.

[21] Appl. No.: 635,310

[22] Filed: Jul. 27, 1984

[30] Foreign Application Priority Data

Jul. 28, 1983 [GB] United Kingdom ............... 8320308

[51] Int. Cl.$^4$ ................. A61K 31/44; C07D 213/59
[52] U.S. Cl. ................. 514/357; 514/183; 514/210; 514/212; 514/218; 514/229; 514/255; 514/318; 514/326; 514/330; 514/332; 514/336; 514/343; 514/422; 514/423; 514/438; 514/444; 514/471; 514/583; 540/575; 540/596; 540/597; 540/598; 540/602; 540/607; 544/131; 544/146; 544/160; 544/360; 544/379; 544/390; 546/2; 546/193; 546/212; 546/226; 546/267; 546/275; 546/281; 546/283; 546/331; 548/527; 548/538; 549/59; 549/60; 564/20; 564/21
[58] Field of Search ............... 564/20, 21; 549/59, 549/60; 546/2, 267, 275, 281, 283, 331; 514/357

[56] References Cited

U.S. PATENT DOCUMENTS

| | | | |
|---|---|---|---|
| 2,678,295 | 5/1954 | Goreau et al. | 564/20 X |
| 3,591,636 | 7/1971 | Houlihan et al. | 564/20 X |
| 3,712,914 | 1/1973 | Tilles | 564/20 X |
| 3,776,942 | 12/1973 | Miller et al. | 564/21 X |
| 4,447,427 | 5/1984 | Klayman et al. | 546/331 X |

FOREIGN PATENT DOCUMENTS 1058835 2/1967 United Kingdom .

OTHER PUBLICATIONS

Clark et al., J. Med. Chem., vol. 22 (1979), p. 1369.
Holmgren, Current Topics in Cellular Regulation, vol. 19 (1981), pp. 47-77.
Elford et al., Cancer Research, vol. 39 (1979), pp. 844-851.
Sartorelli et al., Adv. Eng. Reg., vol. 15 (1977), pp. 117-139.
French et al., J. Med. Chem., vol. 17, No. 2 (1974), pp. 172-180.
Shipman et al., Antimicrobial Agents & Chemotherapy, vol. 19, No. 4 (1981), pp. 682-685.
Cory et al., Cancer Research, vol. 40, (1980), pp. 3891-3894.
Neidhart et al., Cancer Treatment Reports, vol. 64, Nos. 2 & 3 (1980), pp. 251-255.
Kaufman et al., Cancer Chemotherapy Reports, Part 1, vol. 59, No. 5 (1975), pp. 1007-1014.
Cory et al., Cancer Research, vol. 36 (1976), pp. 3166-3170.
Cory et al., Biochemical Pharm., vol. 28, (1979), pp. 867-871.
Brockman et al., Cancer Research, vol. 30 (1970), pp. 2358-2368.
Cheng et al., Antimicrobial Agents and Chemotherapy, vol. 20, No. 3 (1981), pp. 420-423.
De Clercq et al., Proc. Natl. Acad. Sci., vol. 76, No. 6 (1979), pp. 2947-2951.
Grant et al., Biochem. Pharm., vol. 31, No. 6 (1982), pp. 1103-1108.
De Clercq et al., Biochem. Pharm., vol. 28 (1979), pp. 3249-3254.
Dobek et al., Arzheim Forsch, Drug Res., 33 (1983), pp. 1583-1591.

Primary Examiner—Richard L. Raymond  
Attorney, Agent, or Firm—Donald Brown

[57] ABSTRACT

A class of novel thiosemiarbazones has been found to be active against a number of protozoa which cause serious diseases, mainly in the tropical areas of the world.

5 Claims, No Drawings

2-ACETYLPYRIMIDINE-5-[(DIMETHYLAMINO)-THIOCARBONYL]THIOCARBONOHYDRAZONE AND SALTS THEREOF

The present invention relates to thiosemicarbazone compounds having valuable antimicrobial properties, particularly but not exclusively, against protozoa.

Parasite protozoal diseases of man occur throughout the world, often in the tropics, where they are a serious menace to health. Research into the treatment of many of the diseases arising from infections by these parasites has been relatively limited in the past, due to their geographic distribution and incidence. This does not make them any less serious, however.

In Africa, the disease known as trypanosomiasis (sleeping sickness), caused by members of the genus Trypanosoma, exists in chronic (T. gambiense) and acute (T. rhodesiense) forms. In the early stages of both diseases, the parasite is principally free in the blood circulatory system; in late stages, trypanosomes are present in the cerebro-spinal fluid. This causes brain damage, coma and possible death (especially T. rhodesiense). In the early stages of both diseases, treatment with drugs such as suramin and pentamidine is possible; once the CNS is infected, only organic arsenicals such as Mel B can be used. These are highly toxic drugs with low chemotherapeutic indices and require hospitalization of the patient.

In Latin American, a related parasite, Trypanosoma cruzi, causes Chagas' disease. The infection is transmitted by various species of triatomid bug and in its early acute stage is often fatal, if untreted, in young children. Where this is not the case, the disease enters a chronic phase which may last 20 years or more. The protozoan replicates slowly in the heart and/or alimentary tract causing various forms of heart disease and disturbances of the gastro-intestinal tract (especially mega-oesophagus and mega-colon). Acute cases can usually be successfully treated with nifurtimax and benznidazole. Chronic cases respond less well; the drugs are not well tolerated over the time scale (60–120 days) they have to be administered, and there are geographic variations in success rates, these being highest in the South and lowest in the North of Latin America.

In contrast to the trypanosomes, leishmaniasis is prevalent around the world, household pets and wild rodents often acting as reservoirs of infection. It too is caused by a parasite protozoan: Leishmania tropica causes the cutaneous disease; L. donovani the visceral variety (Kala-azar). The parasite replicates in macrophages, particularly those in the skin and liver and spleen. The cutaneous variety can be cured with antimonials such as pentostam; in the visceral disease, pentamidine is often used instead.

Giardiasis (lambliasis) is a gastro-intestinal infection caused by the protozoan Giardia lamblia. It is pandemic, affecting about 10% of the world population, especially children. The condition tends to be chronic, rather than fatal. Symptoms that may occur are usually diarrhoea, often severe, and epigastric pains. Severe cases may result from gallbladder infections, leading to jaundice, nausea and vomiting. Treatment is currently usually with metronidazole; radical cure is not easily attained.

Another 'protozoal' disease of increasing importance is Pneumocystis carinii pneumonia (PCP). This disease commonly occurs in those suffering from acquired immune deficiency syndrome (AIDS); previously it was usually seen only as a highly contagious infantile pneumonia. It is becoming increasingly common in the United States amongst male homosexual communities. It responds to drugs such as pentamidine but cure is difficult.

The filarial diseases of man amount to more than 200 million cases, world wide and are caused by parasite helminths (worms) of the genera Wuchereria, Brugia, Onchocerca and Loa. Such diseases can be controlled by drugs such as diethylcarbamazine and suramin, but such drugs are not always effective and side effects can be severe.

We have now found that certain thiosemicarbazones described below have activity against the above-mentioned organisms. These compounds also have the advantage that they are generally less toxic than many chemotherapeutic agents hitherto used for the treatment of the disease caused by these organisms.

The present invention therefore provide compounds of formula (I)

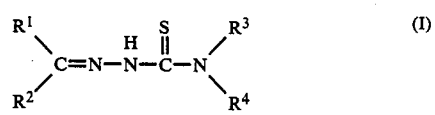

wherein $R^1$ represents an unsubstituted phenyl, thienyl or pyridyl group; a thienyl, pyridyl or phenyl group substituted by at least one (e.g., 1, 2 or 3) substituent selected from $C_{1-6}$ alkyl (e.g., methyl or ethyl), $C_{1-6}$ alkoxy (e.g., methoxy or ethoxy), amino, hydroxy, halo (chloro, bromo, iodo or fluoro) and nitro radicals; or a 2-pyridyl group further substituted in the 6-position by a group of formula $-C(R^2)=N-NH-CS-NR^3R^4$ (wherein $R^2$, $R^3$ and $R^4$ are hereinafter defined); $R^2$ represents a hydrogen atom or a $C_{1-6}$ alkyl (e.g., methyl) group; $R^3$ represents a hydrogen atom, a $C_{1-6}$ alkyl (e.g., methyl or ethyl) group, a group of formula Z-X (wherein Z represents a $C_{1-4}$ straight or branched alkylene group and X represents a $C_{1-6}$ alkoxy group, a phenyl group substituted by at least one $C_{1-6}$ alkoxy group, or a 5- or 6-membered heterocyclic ring containing at least one heteroatom selected from oxygen, nitrogen and sulphur, e.g., a 2-, 3- or 4-pyridyl, morpholino or 2-, 3- or 4-furanyl group), or a group of formula

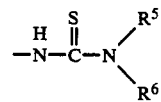

(wherein $R^5$ and $R^6$, which may be the same or different, each representing a hydrogen atom or $C_{1-6}$ alkyl group); and $R^4$ represents a hydrogen atom or a $C_{1-6}$ alkyl group; or $R^3$ and $R^4$ together with the nitrogen atom to which they are attached form a 3- to 7-membered alkyleneimino ring (optionally containing a double bond) or a homopiperazino, piperazino or morpholino group optionally containing 1, 2 or 3 substituents selected from $C_{1-4}$ alkyl, hydroxy, phenyl and benzyl.

It will be appreciated by those skilled in the art of organic chemistry that some of the compounds of formula (I) can form salts or can form complexes with metals. Such salts and complexes are encompassed in the scope of this invention.

Preferred compounds of formula (I) include those wherein $R^1$ represents a pyridyl or thienyl group (preferably a 2-pyridyl or 2-thienyl group) or a phenyl group optionally substituted in the 2-position by a substituent selected from $C_{1-6}$ alkoxy (e.g. methoxy), hydroxy and amino radicals or in the 3-position by a nitro substituent and if desired by one or more further substituents, e.g. $C_{1-6}$ alkyl (e.g. methyl) or hydroxy radicals, e.g. in the 3-, 4-, 5- and/or 6-positions, or a 2-pyridyl group further substituted in the 6-position by a group of formula

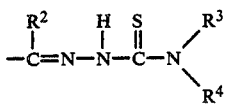

(wherein $R^2$, $R^3$ and $R^4$ are as hereinafter defined);

$R^2$ represents a hydrogen atom or a $C_{1-6}$ alkyl (e.g. methyl) group;

$R^3$ represents a $C_{1-6}$ alkyl (e.g. methyl or tert-butyl) group; a group of formula —Z—X (wherein Z represents a $C_{1-4}$ straight or branched alkylene group, e.g. a methylene group) and X represents a phenyl group substituted by at least one $C_{1-6}$ alkoxy group (e.g. a methoxy group) or a 5- or 6-membered heterocyclic ring containing at least one heteroatom selected from oxygen, nitrogen and sulphur, e.g. a 2-, 3- or 4-pyridyl, morpholino or 2-, 3- or 4-furanyl group); a diphenyl methyl group; or a group of formula

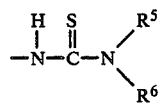

(wherein $R^5$ and $R^6$ which may be the same or different, each represents a hydrogen atom or a $C_{1-6}$ alkyl group e.g. methyl group); and $R^4$ represents a hydrogen atom or a $C_{1-6}$ alkyl group.

Particularly preferred compounds having generally high anti-microbial activity particularly against one or more of the above-mentioned parasites include:

(1) 2′-Aminoacetophenone 4,4-dimethylthiosemicarbazone
(2) 2-Acetylpyridine 4-tert-butylthiosemicarbazone
(3) 2-Acetylpyridine 4-furfurylmethylthiosemicarbazone
(4) 2-Acetylpyridine 4-(2-morpholinoethyl)thiosemicarbazone
(5) 2-Acetylpyridine 4-(3,4,5-trimethoxybenzyl)thiosemicarbazone
(6) 2′-Hydroxyacetophenone 4,4-dimethylthiosemicarbazone
(7) 2-Acetylpyridine 4-benzhydrylthiosemicarbazone
(8) 2,6-Diacetylpyridine bis(4,4-dimethylthiosemicarbazone)
(9) 2-Acetylthiophene 4,4-dimethylthiosemicarbazone
(10) 2-Acetylpyridine 5-[(dimethylamino)thiocarbonyl]thiocarbonohydrazone
(11) 3′-Nitroacetophenone 4,4-dimethylthiosemicarbazone
(12) 2-Acetylthiophene 5-(dimethylthiocarbamoyl)thiocarbonohydrazone
(13) 2′,3′-Dihydroxybenzaldehyde 4,4-dimethylthiosemicarbazone
(14) 2′-Hydroxybenzaldehyde 4,4-dimethylthiosemicarbazone
(15) 2′-Hydroxy-5′-methylacetophenone 4,4-dimethylthiosemicarbazone
(16) Acetophenone 4,4-dimethylthiosemicarbazone
(17) 2′-Hydroxy-4′,6′-dimethylacetophenone 5-(N,N-dimethylthiocarbamoyl)thiocarbonohydrazone
(18) 2′-Hydroxyacetophenone 4-tert-butylthiosemicarbazone
(19) 2′-Methoxyacetophenone 4,4-dimethylthiosemicarbazone
(20) 2′-Hydroxy-4′,5′-dimethylacetophenone 4,4-dimethylthiosemicarbazone
(21) 2-Acetylpyridine 4-(3-morpholinopropyl)thiosemicarbazone
(22) 2-Acetylpyridine 4-[2-(2-pyridyl)ethyl]thiosemicarbazone
(23) 2-Acetylpyridine 4,4-(dimethylthiosemicarbazonato)copper (II) bisulfate
(24) 2′,3′-Dihydroxyacetophenone 4-(2-morpholinoethyl)thiosemicarbazone
(25) 2′-Hydroxy-5′-methylacetophenone 4-(2-morpholinoethyl)thiosemicarbazone
(26) 2′,5′-Dihydroxyacetophenone 4-(2-morpholinoethyl)thiosemicarbazone Compounds 4, 6 and 10 above have been found to be especially active in in vitro tests against P. carinii, the activity of compound 6 being especially high.

Compound 3, 4, 5, 6, 9, 10, 12, 21 and 22 have besen found to have activity against the filarial organism Brugia pahangi, some compounds with the advantage that they have a relatively low toxicity. Certain of the compounds of formula (I) are also active sagainst Babesia, e.g. B. rodhaini, especially compound 23. Also, compounds 24, 25 and 26 have been found to be active against P. falciparum.

The present invention thus provides the novel compounds of formula (I) identified above.

The compounds of formula (I) may be prepared in conventional manner by techniques known in the art, for example by reacting a compound of formula

(wherein $R^1$ and $R^2$ are as defined above) with a compound of formula

(wherein $R^3$ and $R^4$ are as defined above).

The reaction is advantageously effected in an appropriate solvent medium, e.g. methanol, ethanol, 2-dichloroethane, if desired in the presence of glacial acetic acid.

The present invention further provides the above compounds of formula (I) for use in therapy, for example in the treatment or prophylaxis of microbial infections in humans or animals, particularly infections caused by protozoal organisms such as L. donovani, T. cruzi or T. gambiense, P. falciparum and B. rodhaini, helminth organisms such as *B. pahangi* and other organisms such as *P. carinii*.

The present invention also provides a method for the treatment or prophylaxis of a microbial infection, e.g., as described above which comprises administering to a human or non-human host an effective anti-microbial amount of a compound of formula (I).

The compounds of formula (I) hereafter referred to as the active ingredient(s) may be administered by any route appropriate to the condition to be treated, suitable routes including oral, rectal, nasal, topical (including subcutaneous, intramuscular, intravenous, intradermal, intrathecal and epidural). It will be appreciated that the preferred route may vary with, for example, the condition of the recipient.

For each of the above-indicated utilities and indications the amount required of an active ingredient (as above defined) will depend upon a number of factors including the severity of the conditions to be treated and the identity of the recipient and will ultimately be at the discretion of the attendant physician or veterinarian. In general, however, for each of these utilities and indications, a suitable, effective dose will be in the range 0.1 to 250 mg per kilogram bodyweight of recipient per day, preferably in the range 1 to 100 mg/kg bodyweight per day and most preferably in the range 5 to 20 mg/kg bodyweight per day. The desired dose may be presented as two, three, four or more sub-doses administered at appropriate intervals throughout the day. These sub-doses may be administered in unit dosage forms, for example, containing 10 to 100 mg, preferably 20 to 500 mg and most preferably 100 to 400 mg of active ingredient per unit dosage form.

While it is possible for the active ingredients to be administered alone it is preferable to present them as pharmaceutical formulations. The formulations, both for veterinary and for human use, of the present invention comprise at least one active ingredient, as above defined, together with one or more acceptable carriers therefor and optionally other therapeuti ingredients. The carrier(s) must be "acceptable" in the sense of being compatible with the other ingredients of the formula and not deleterious to the recipient thereof.

The formulations include those suitable for oral, rectal, nasal, topical (including buccal and sublingual), vaginal or parenteral (including subcutaneous, intramuscular, intravenous, intradermal, intrathecal andd epidural) administration. The formulations can conveniently be presented in unit dosage form and may be prepared by any of the methods will known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing predetermined amounts of the active ingredients; as a powder or granules; as solutions or suspensions in an aqueous liquid or a non-aqueous liquid; or as oil-in-water emulsions or water-in-oil liquid emulsions. The active ingredient may also be presented as a bolus electuary or paste.

A tablet may be made by compression or moulding, optionally with one or more accessory ingredients. Compressed tablets may be prepared by compressing in a suitable machine the active ingredients in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues, e.g., mouth and skin, the formulations are preferably applied as a topical ointment or cream containing the antiviral active ingredient in an amount of, for example, 0.075 to 20% w/w, preferably 0.2 to 15% w/w and most preferably 0.5 to 10% w/w. When formulated in an ointment, the active ingedients may be employed with either paraffinic or a water-miscible ointment base. Alternatively, the active ingredients may be formulated in a cream with an oil-in-water cream base.

Formulations suitable for topical administration to the eye also include eye drops wherein the active ingredients are dissolved or suspended in suitable carrier, especially an aqueous solvent for the active ingredient. The antiviral active ingredient is preferably present in such formulations in a concentration of 0.5 to 20%, advantageously 0.5 to 10% particularly about 1.5% w/w.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in a manner in which snuff is taken, i.e., by rapid inhalation through the nasal passage from a container of the powder held close up to the nose. Suitable formulations wherein the carrier is a liquid, for administration as for example a nasal spray or as nasal drops, include aqueous or oil solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solution and suspensions may be prepared from sterile powders, granules and tablets of the kind previously described.

Preferred unit dosage formulations are those containing a daily dose or unit daily sub-dose, as herein above recited, or an appropriate fraction thereof, of the active ingredients.

It should be understood that in addition to the ingredients particularly mentioned above the formulations of this invention may include other agents conventional in the art having regard to the type of formulation in question, for example those suitable for oral administration may include flavouring agents.

The following Examples are for illustration only and are not intended to limit the scope of the invention in any way.

EXAMPLES (a) Preparation of Thiosemicarbazones

General procedure: The appropriate aldehyde or ketone (A) and 4-substituted thiosemicarbazide (B) were refluxed in the specified reaction medium until the reaction was complete. The solid product was collected by filtration of the cooled reaction mixture and was then purified by recrystallization from the specified solvent or by column chromatography on silica gel followed by recrystallization from the specified solvent. Appropriate modifications are indicated in the Table below.

A specific example is:

2-Acetylpyridine 4-(2-morpholinoethyl)thiosemicarbazone

A mixture of 6.00 g (0.0294 mole) of 4-(2-morpholinoethyl)thiosemicarbazide, 3.91 g (0.0323 mole) of 2-acetylpyridine, 20 mL of 95% ethanol, and 0.4 mL of glacial acetic acid was heated under reflux for 1.25 hours. The mixture then stood overnight at room temperature. Colourless crystals were collected and recrystallised from 40 mL of 95% ethanol; yield 7.81 g (86%) of pale yellow crystals of 2-acetylpyridine 4-(2-morpholinoethyl)thioseicarbazone, mp 167.5°–169° C.

| Analysis for $C_{14}H_{21}N_5OS$: | | | |
|---|---|---|---|
| Calculated | C: 54.69 | H: 6.89 | N: 22.78 |
| Found | C: 54.66 | H: 6.86 | N: 22.88 |

Exceptions to the general procedure were the preparations of the thiocarbonylthiocarbonohydrazones:

2-Acetylpyridine 5-[(dimethylamino)thiocarbonyl]thiocarbonohydrazone

A mixture of 24.2 g (0.203 mole) of 4,4-dimethylthiosemicarbazide, 26.6 g (0.220 mole) of 2-acetylpyridine, 2.5 mL of glacial acetic acid, and 100 mL of 95% ethanol was refluxed for 1.5 hours. The mixture was incubated overnight at room temperature. Thick orange needles contaminated with a little light-coloured solid were collected, washed with 20 mL of ethanol, and while still damp were added to 450 mL of boiling methanol. After the orange needles dissolved (less than 10 minutes) the mixture was filtered, and the undissolved solid was boiled again with methanol (50 mL) for three minutes. The mixture stood for 0.25 hour at room temperture, then the yellow crystals were collected by filtration; yield 1.47 g (5%) of 2-acetylpyridine 5-[(dimethylamino)thiocarbonyl]thiocarbonohydrazone, mp 152.5° C., (evolved a gas, resolidified, and remelted at 175°–181.5°).

| Analysis for $C_{11}H_{16}N_6S_2$. | | | |
|---|---|---|---|
| Calculated | C: 44.57 | H: 5.44 | N: 28.35 |
| Found | C: 44.75 | H: 5.52 | N: 28.45 |

2'-Hydroxy-4',6-dimethylacetophenone 5-(N,N-dimethylthiocarbamoyl)thiocarbonohydrazone A mixture of 4,4-dimethyl-3-thiosemicarbazide (1.79 g, 0.015 mol), 2-hydroxy-4,6-dimethylacetophenone (2.71 g, 0.0165 mol), glacial acetic acid (0.5 ml) and 95% EtOH (30 ml) was refluxed for 2 h. The resulting solution was concentrated under vacuum to a dark golden oil determined by TLC (silica/hexanes:EtOAc) to be a mixture. This mixture was subjected to liquid chromatography on silica gel (Merck Kieselgel 60; 230–400 mesh ASTM) with gradient elution (hexane-EtOAc). The product, eluted by 100% EtOAc and twice recrystallized from EtOAc:hexane, was isolated as an isomeric mixtue (based on NMR): yield 0.87 g (17%); mp 158° C. (dec).

| Analysis for $C_{14}H_{21}N_5OS_2$: | | | |
|---|---|---|---|
| Calculated | C: 49.52 | H: 6.23 | N: 20.63 | S: 18.89 |
| Found | C: 49.52 | H: 6.34 | N: 20.54 | S: 18.84 |

2-Acetylthiophene 5-(N,N-dimethylthiocarbamoyl)thiocarbonohydrazone

A mixture of 2-acetylthiophene (5.04 g, 0.040 mol), 4,4-dimethylthiosemicarbazide (2.98 g, 0.025 mol), 95% EtOH (20 mL) and glacial HOAc (0.4 mL) was refluxed for 1 h. The resulting solution was allowed to stand overnight at ambient temperature. The crystals that had separated were subsequently collected by filtration, washed with boiling 95% EtOH (30 mL), and recrystallized from 95% EtOH: yield, 0.48 g (13%) of 2-acetylthiophene 5-(N,N-dimethylthiocarbamoyl)thiocarbonohydrazone, mp 161° C., then resolidified.

| Analysis for $C_{10}H_{15}N_5S_3$: | | | |
|---|---|---|---|
| Calculated | C: 39.84 | H: 5.02 | N: 23.23 | S: 31.91 |
| Found | C: 39.86 | H: 5.04 | N: 23.16 | S: 31.86 |

2,6-Diacetylpyridine bis-(4,4-dimethylthiosemicarbazone)

A mixture of 4,4-dimethylthiosemicarbazide (2.70 g, 0.022 mol) and 2,6-diacetylpyridine (1.63 g, 0.10 mol) in 95% EtOH (45 ml) containing glacial acetic acid (0.5 ml) was heated by a steam bath for 1 h and 10 min and allowed to cool to ambient temperature. The yellow precipitate was collected by filtration, washed with 95% EtOH, and subsequently recrystallized from toluene: yield 2.72 g (73%); mp 215° (dec).

| Analysis for $C_{15}H_{23}N_7S_2.0.10\ C_7H_8$: | | | |
|---|---|---|---|
| Calculated | C: 50.31 | H: 6.40 | N: 26.17 | S: 17.11 |
| Found | C: 50.26 | H: 6.20 | N: 26.12 | S: 17.27 |

2-Acetylpyridine 4,4-(dimethylthosemicarbazonato)copper (II) 7/10 bisulfate 3/10 hydroxide hemihydrate A solution of 2-acetylpyridine 4,4-dimethylthosemicarbazone (0.500 g, 0.00225 mol) in MeOH (100 ml) at ambient temperature was added to a stirred solution of cupric sulfate pentahydrate (0.560 g, 0.00225 mol) in MeOH (75 ml). After 0.5 h, the solution was concentrated by boiling to 75 ml and was subsequently chilled. The dark crystals that separated were collected by filtration and washed with methanol: yield 0.42 g (51%), mp 242°–244° (dec).

| Analysis for $C_{10}H_{13}CuN_4S.7/10HSO_4.3/10\ OH.\frac{1}{2}\ H_2O$: | | | | |
|---|---|---|---|---|
| Calculated | C: 32.74 | H: 4.12 | N: 15.27 | S: 14.85 |
| | Cu: 17.32 | | | |
| Found | C: 32.81 | H: 4.14 | N: 15.02 | S: 15.14 |
| | Cu: 17.23 | | | |

THE FOLLOWING EQUATION APPLIES TO THE TABLE SHOWN BELOW:

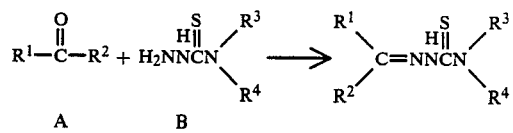

PREPARATION OF THIOSEMICARBAZONES

| $R^1$ | $R^2$ | $R^3$ | $R^4$ | Molar Ratio A/B | Reaction Medium$^a$ | Reaction Time (hr) | Recrystallization Solvent | Yield (%) | mp (°C.) |
|---|---|---|---|---|---|---|---|---|---|
| 2-pyridyl | Me | $-(CH_2)_3-N\diagup\diagdown O$ (morpholino) | H | 1.9 | $ClCH_2CH_2Cl$ | 3 | i-PrOH | 47 | 126.5–127 |
| 2-pyridyl | Me | $-(CH_2)_2$-(2-pyridyl) | H | 1.1 | 95% EtOH/ 5% glacial acetic acid | 1½ | Toluene | 71 | 125–127 |
| 2-pyridyl | Me | $-CMe_3$ | H | 1.0 | $ClCH_2CH_2Cl$ | ¾ | i-PrOH | 42 | 118–120.5 |
| 2-pyridyl | Me | $-CH_2$-(2-furyl) | H | 1.05 | $ClCH_2CH_2Cl$ | 1¼ | i-PrOH | 75 | 149 |
| 2,3-dihydroxyphenyl (HO, OH) | H | Me | Me | 1.1 | EtOH/2% HOAc | 1½ | 95% EtOH | 71 | 206–207 (dec) |
| 2-pyridyl | Me | $-CH_2$-(3,4,5-trimethoxyphenyl) | H | 1.1 | EtOH/5% HOAc | 1.5 | 95% EtOH | 80 | 163–164 |
| 2-hydroxyphenyl | H | Me | Me | 1.1 | EtOH/2% HOAc | 2 | 95% EtOH | 76 | 199–200 (dec) |
| 4-methyl-2-hydroxyphenyl | Me | Me | Me | 1.1 | EtOH/2% HOAc | 1.5 | * | 85 | 217–217.5 (dec) |
| 2-methoxyphenyl | Me | Me | Me | 1.1 | EtOH/2% | 6 | * | 39 | 159–160 |

-continued

PREPARATION OF THIOSEMICARBAZONES

| R$^1$ | R$^2$ | R$^3$ | R$^4$ | Molar Ratio A/B | Reaction Medium$^a$ | Reaction Time (hr) | Recrystallization Solvent | Yield (%) | mp (°C.) |
|---|---|---|---|---|---|---|---|---|---|
| 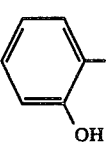 2-hydroxyphenyl | Me | C—Me$_3$ | H | 1.1 | EtOH/2% HOAc | 17 | EtOH/hexanes$^b$ | 24 | 166–167 |
| 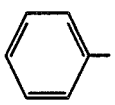 phenyl | Me | Me | Me | 1.1 | EtOH/2% HOAc | 16.5 | 95% EtOH | 19 | 107–108 |
| 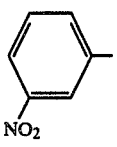 3-nitrophenyl | Me | Me | Me | 1.1 | EtOH/1% HOAc | 1.5 | EtOAc$^c$ | 18 | 164–165 |
| 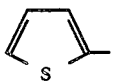 2-thienyl | Me | Me | Me | 0.45 | EtOH/2% HOAc | 1.5 | $^b$ | 7 | 130–131* |
| 2-pyridyl | Me | H—CHPh$_2$— | H | 1.1 | EtOH/2.5% HOAc | 1.5 | Toluene | 88 | 183–185 |
| 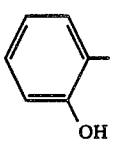 2-hydroxyphenyl | Me | Me | Me | 1 | EtOH/0.4% HOAc | 3.5 | 95% EtOH | 64 | 209–210 |
| 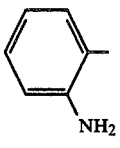 2-aminophenyl | Me | Me | Me | 1.1 | MeOH | 4 | MeOH$^d$ | 4 | 151–153 (dec) |
| 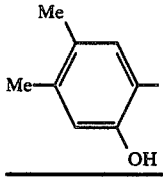 3,5-dimethyl-4-hydroxyphenyl | Me | Me | Me | 1.1 | EtOH/2% | 6 | 95% EtOH | 26 | 234.5–235 (dec) |

*Crystallized analytically pure from the reaction medium
$^a$EtOH refers to 95% ethyl alcohol and HOAc to glacial acetic acid. The percent HOAc is based on weight.
$^b$After lc on silica gel with EtOAc/hexanes
$^c$After fractional crystallisation from the reaction medium
$^d$After lc on silica gel with CH$_2$Cl$_2$

(b) Pharmaceutical Formulations

In the following Examples, the active compound is a compound of formula (I).

| Tablet | Amount (mg) |
|---|---|
| Active Compound | 200 |
| Lactose | 105 |
| Starch | 50 |
| Polyvinylpyrrolidinone | 20 |
| Magnesium Stearate | 10 |

Mix the active compounds with the lactose and starch and wet granulate with a solution of the polyvinylpyrrolidinone. Dry, sift, blend the granules with magnesium stearate and compress.

| Capsule | Amount (mg) |
|---|---|
| Active Compound | 200 |
| Lactose | 100 |
| Sodium Starch Glycollate | 10 |
| Polyvinylpyrrolidinone | 10 |
| Magnesium Stearate | 3 |

Mix the active compounds with the lactose and sodium starch glycollate and wet granulate with a solution of the polyvinylpyrrolidinone. Dry, sift, blend the granules with the magnesium stearate and fill into hard gelatin capsules.

Intravenous Injections

| | | Amount |
|---|---|---|
| (1) | Active Compound | 200 mg |
| | Glycerol | 200 mg |
| | Sodium Hydroxide solution qs | pH 7.0–7.5 |
| | Water for Injections to | 10 mL |

Add the glycerol to some of the water for Injections. Dissolve the active compound and adjust the pH with Sodium Hydroxide solution. Make up to volume with additional Water for Injections. Under aseptic conditions, sterilise the solution by filtration, fill into sterile ampoules and seal the ampoules.

| | | |
|---|---|---|
| (2) | Active Compound | 100 mg |
| | Sodium Hydroxide solution qs to | pH 8.0–9.0 |
| | Mannitol | 125 mg |

| | |
|---|---|
| -continued | |
| Water for Injections to | 2.5 ml |

Dissolve the active compounds and the mannitol in a part of the Water for Injections. Adjust pH with the sodium hydroxide solution and make up to volume with additional Water for Injections. Under aseptic conditions, sterilise with solution by filtration, fill into sterile vials and remove the water by freeze-drying. Seal the vials under an atmosphere of nitrogen and close the vials with a sterile closure and a metal collar.

I claim:

1. 2-Acetylpyridine 5-[(dimethylamino)thiocarbonyl]thiocarbonohydrazone.

2. A salt of 2-Acetylpyridine 5-[(dimethylamino)thiocarbonyl]thiocarbonohydrazone.

3. Isolated 2-Acetylpyridine 5-[(dimethylamino)thiocarbonyl]thiocarbonohydrazone.

4. A topical pharmaceutical preparation comprising the compound of claim 1 together with a pharmaceutically acceptable topical carrier therefor.

5. A topical pharmaceutical preparation comprising the salt of claim 2 together with a pharmaceutically acceptable topical carrier therefor.

* * * * *

UNITED STATES PATENT AND TRADEMARK OFFICE
CERTIFICATE OF CORRECTION

PATENT NO.   :   4,719,221

DATED        :   January 12, 1988

INVENTOR(S)  :   Robert W. Morrison, Jr.

It is certified that error appears in the above-identified patent and that said Letters Patent is hereby corrected as shown below:

In the Abstract, first line, cancel "thiosemiarbazones" and insert --thiosemicarbazones--.

Col. 1, line 33, after "fatal, if", cancel "untreted" and insert --untreated--.

Col. 4, line 30, cancel "Compound" and insert --Compounds--; after "have", cancel "besen" and insert --been--.

Col. 4, line 34, after "active", cancel "sagainst", and insert --against--.

Col. 5, line 40, after "other", cancel "therapeuti" and insert --therapeutic--.

Col. 5, line 47, after "intrathecal", cancel "andd" and insert --and--.

Col. 6, line 17, after "active", cancel "ingedients" and insert --ingredients--.

Col. 8, line 15, cancel "mixtue" and insert --mixture--.

Col. 11, under heading "$R^3$", mid page, cancel "H-CHPh$_2$" and insert --CHPh$_2$--.

UNITED STATES PATENT AND TRADEMARK OFFICE
CERTIFICATE OF CORRECTION

PATENT NO. : 4,719,221

DATED : January 12, 1988

INVENTOR(S) : Robert W. Morrison, Jr.

It is certified that error appears in the above-identified patent and that said Letters Patent is hereby corrected as shown below:

Please change inventors name from "Jr. Morrison" to --Robert W. Morrison, Jr.--.

Col. 4, line 28, "in vitro" should be italicized.

Col. 5, line 50, after "methods", cancel "will" and insert --well--.

Col. 8, line 61, cancel "4,4-(dimethylthosemicarbazonato) copper" and insert --4,4-(dimethylthiosemicarbazonato)copper--; line 64, cancel "thosemicarbazone" and insert --thiosemicarbazone--

Signed and Sealed this

Seventh Day of February, 1989

*Attest:*

DONALD J. QUIGG

*Attesting Officer*   *Commissioner of Patents and Trademarks*